US007439262B1

(12) United States Patent
Dantanarayana et al.

(10) Patent No.: US 7,439,262 B1
(45) Date of Patent: Oct. 21, 2008

(54) SUBSTITUTED 1-ALKYLAMINO-1-H-INDAZOLES FOR THE TREATMENT OF GLAUCOMA

(75) Inventors: Anura P. Dantanarayana, Kandy (LK); Jesse A. May, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/950,598

(22) Filed: Dec. 5, 2007

Related U.S. Application Data

(62) Division of application No. 11/012,552, filed on Dec. 15, 2004, now Pat. No. 7,338,972.

(60) Provisional application No. 60/529,687, filed on Dec. 15, 2003.

(51) Int. Cl.
*A61K 31/416* (2006.01)
*C07D 231/56* (2006.01)
(52) U.S. Cl. .................... 514/406; 548/361.1
(58) Field of Classification Search .......... 514/406; 548/361.1
See application file for complete search history.

(56) References Cited

U.S. PATENT DOCUMENTS

| 4,690,931 | A | 9/1987 | Wick et al. | 514/317 |
| 5,011,846 | A | 4/1991 | Gittos et al. | 514/294 |
| 5,151,444 | A | 9/1992 | Ueno et al. | 514/530 |
| 5,290,781 | A | 3/1994 | Espino et al. | 514/259 |
| 5,296,504 | A | 3/1994 | Stjernschantz et al. | 514/530 |
| 5,352,708 | A | 10/1994 | Woodward et al. | 514/729 |
| 5,422,368 | A | 6/1995 | Stjernschantz et al. | 514/530 |
| 5,494,928 | A | 2/1996 | Bös | 514/415 |
| 5,538,974 | A | 7/1996 | Ogawa et al. | 514/253 |
| 5,561,150 | A | 10/1996 | Wichmann | 514/406 |
| 5,571,833 | A | 11/1996 | Kruse et al. | 514/414 |
| 5,578,612 | A | 11/1996 | Macor et al. | 514/323 |
| 5,646,173 | A | 7/1997 | Bös | 514/411 |
| 5,652,272 | A | 7/1997 | Ogawa et al. | 514/652 |
| 5,693,654 | A | 12/1997 | Birch | 514/323 |
| 5,760,028 | A | 6/1998 | Jadhav et al. | 514/211 |
| 5,874,477 | A | 2/1999 | McConnell et al. | 514/657 |
| 5,889,052 | A | 3/1999 | Klimko et al. | 514/530 |
| 5,902,815 | A | 5/1999 | Olney et al. | 514/285 |
| 6,107,324 | A | 8/2000 | Behan et al. | 514/406 |
| 6,660,870 | B1 | 12/2003 | Ruskinko et al. | 548/307.4 |
| 6,664,286 | B1 | 12/2003 | May et al. | 514/415 |
| 6,696,476 | B2 | 2/2004 | Chen et al. | 514/403 |
| 6,806,285 | B1 | 10/2004 | May et al. | 514/416 |
| 6,884,816 | B2 | 4/2005 | May et al. | 514/405 |
| 6,933,392 | B2 | 8/2005 | May et al. | 514/406 |
| 7,338,972 | B1 * | 3/2008 | Dantanarayana et al. | 514/406 |

FOREIGN PATENT DOCUMENTS

| EP | 0 771 563 B1 | 1/2003 |
| WO | WO 92/00338 | 1/1992 |
| WO | WO 94/03162 | 2/1994 |
| WO | WO 94/13275 | 6/1994 |
| WO | WO 97/35579 | 10/1997 |
| WO | WO 98/18458 | 5/1998 |
| WO | WO 98/31354 | 7/1998 |
| WO | WO 99/59499 | 11/1999 |
| WO | WO 00/12475 | 3/2000 |
| WO | WO 00/12510 | 3/2000 |
| WO | WO 00/35922 | 6/2000 |
| WO | WO 00/44753 | 8/2000 |
| WO | WO 00/77002 | 12/2000 |
| WO | WO 00/77010 | 12/2000 |
| WO | WO 01/40183 | 6/2001 |
| WO | WO 01/70207 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 01/85152 | 11/2001 |
| WO | WO 02/40456 | 5/2002 |
| WO | WO 02/098350 | 12/2002 |
| WO | WO 02/098400 | 12/2002 |
| WO | WO 02/098860 | 12/2002 |
| WO | WO 03/000663 | 1/2003 |
| WO | WO 03/051291 | 6/2003 |
| WO | WO 03/051352 | 6/2003 |
| WO | WO 03/053436 | 7/2003 |
| WO | WO 2004/019874 | 3/2004 |
| WO | WO 2004/028451 | 4/2004 |
| WO | WO 2004/054572 | 7/2004 |
| WO | WO 2004/058725 | 7/2004 |

OTHER PUBLICATIONS

Antonini et al., "Synthesis, Antitumor Cytotoxicity, and DNA-Binding of Novel N-5,2-Di(α-aminoalkyl)-2,6-dihydropyrazolol[3,4,5-kl]acridine-5-carboxamides," *J. Med. Chem.*, vol. 44, pp. 3329-3333 (2001).

Antonini et al., 2,6-Di(α-aminoalkyl)-2,5,6,7-tetrahydropyrazolol[3,4,5-mn]pyrimido[5,6,1-de]-acridine-5,7-diones: Novel, Potent, Cytotoxic, and DNA-Binding Agents, *J. Med. Chem.*, vol. 45, pp. 696-702 (2002).

Barben et al., "Heterocyclic Fluorine Compounds. Part IV. Monofluoroindazoles," *J. Chem. Soc.*, p. 672 (1960).

Batt et al., "Disubstituted Indazoles as Potent Antagonists of the Integrin $\alpha_v\beta_3$," *J. Med. Chem.*, vol. 43, pp. 41-58 (2000).

Bowen et al., "Nonlinear regression using spreadsheets," *Trends In Pharmacological Sciences*, vol. 16, pp. 413-423 (1995).

Chang et al., "Mechanism of the Ocular Hypotensive Action of Ketanserin," *J. of Ocular Pharmacology*, vol. 1(2), pp. 137-147 (1985).

Johnson et al., "Binding to the Serotonin 5-Ht$_2$ Receptor by the Enantiomers of $^{125}$I-DO," *Neuropharmacology*, vol. 26(12), pp. 1803-1806 (1987).

(Continued)

*Primary Examiner*—Kamal A Saeed
(74) *Attorney, Agent, or Firm*—Patrick M. Ryan

(57) ABSTRACT

Substituted 1-alkylamino-1H-indazoles for lowering intraocular pressure and treating glaucoma are disclosed.

7 Claims, No Drawings

OTHER PUBLICATIONS

Krootila et al., "Effect of Serotonin and Its Antagonist (Ketanserin) on Intraocular Pressure in the Rabbit," *J. of Ocular Pharmacology*, vol. 3(4), pp. 279-290 (1987).

Mallorga et al., "Characterization of Serotonin Receptors in the Iris + ciliary body of the albino rabbit," *Current Eye Research*, vol. 6(3), pp. 527-532 (1987).

Mano et al., "The Effect of Anplag (Sarpogelate HCL), New Selective 5-$HT_2$ Antagonist on Intraocular Pressure in Rabbits," *IOVS*, vol. 36(4), S719 (1995).

May et al., "A Novel and Selective 5-$HT_{2\,Receptor}$ Agonist with Ocular Hypotensive Activity: (S)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotensive Response of Serotonin 5-$HT_{1A}$ and 5-$HT_2$ Receptor Ligands in Conscious Ocular Hypertensive Cynomolgus Monkeys," *J. of Pharmacology and Experimental Therapeutics*, vol. 306(1), pp. 301-309 (2003).

Osborne et al., "Do Beta-Adrenoceptors and Serotonin 5-$HT_1A$ Receptors have Similar Functions in the control of Intraocular Pressure in the Rabbit?", *Ophthalmologica*, vol. 210, pp. 308-314 (1996).

Osborne et al., "5-Hydroxytryptamine$_{1A}$ agonists: potential use in glaucoma. Evidence from animal studies," *Eye*, vol. 14(38), pp. 454-463 (2000).

Takeda et al., "The Effect of Inplag. Novel Selective 5-$HT_2$ Antagonist on Intraocular Pressure in Glaucoma Patients," IOVS, Vo. 36(4), S734 (1995).

Wang et al., "Effect of 5-methylurapidil, an $\alpha_{1a}$-adrenergic antagonist and 5-hydroxytryptamine$_{1a}$ agonist, on aqueous humor dynamics in monkeys and rabbits," *Current Eye Research*, vol. 16(8), pp. 769-775 (1997).

Wang et al., "Effect of $_p$-MPPI Hydrochloride (p-MPPI) Applied before 5-methylurapidil (5-MU) on Intraocular Pressure (IOP) in Normal Monkeys," *IOVS*, vol. 39(4) (1998).

* cited by examiner

SUBSTITUTED 1-ALKYLAMINO-1-H-INDAZOLES FOR THE TREATMENT OF GLAUCOMA

RELATED APPLICATIONS

This application is a divisional of U.S. application Ser. No. 11/012,552, filed Dec. 15, 2004, now U.S. Pat. No. 7,338,972 which claims priority from U.S. Application No. 60/529,687, filed Dec. 15, 2003, the entire contents of which are incorporated herein by reference.

BACKGROUND OF THE INVENTION

The present invention relates to the use of substituted 1-alkylamino-1H-indazoles for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Opthalmologica, Vol. 210:308-314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769-775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but attribute the IOP effect to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see U.S. Pat. No. 6,664,286 which is incorporated in its entirety. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives, and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. WO 02/40456 and WO 03/00663 relate to certain substituted 1-(pyrazinyl)-piperazines and substituted 1-(pyrimidinyl)-piperazines, respectively, as agonists or antagonists at 5-$HT_{2C}$ receptors for the treatment of a variety of central nervous system related disorders, especially obesity and sexual dysfunction. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

Few substituted 1-(2-aminoethyl)-1H-indazole-6-carboxylic acid compounds have been reported. Antonini et al, J. Med. Chem. 45, 696 (2002) and 44, 3329 (2001) have reported tetra- and penta-cyclic heterocyclic compounds which have embedded within their complex framework the structural elements of 1-(2-aminoethyl)-1H-indazole-6-carboamides. U.S. Pat. No. 5,760,028 broadly discloses indazolecarboxamide compounds which can include certain unexemplified substituted indazole-6-carboxamides as integrin receptor antagonists. However, these compounds are unlike the compounds of the present application by virtue of the dissimilar substituents on the indazole.

All the patents and publications mentioned above and throughout are incorporated in their entirety by reference herein.

5-Hyroxytryptamine (serotonin) does not cross the blood-brain barrier and enter the brain. However, in order to increase brain serotonin levels the administration of 5-hydroxy-tryptophan can be employed. The transport of 5-hydroxy-tryptophan into the brain readily occurs, and once in the brain 5-hydroxy-tryptophan is rapidly decarboxylated to provide serotonin. Serotonin, however, is non-selective and unstable.

Accordingly, there is a need to provide new compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are 5-HT$_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I:

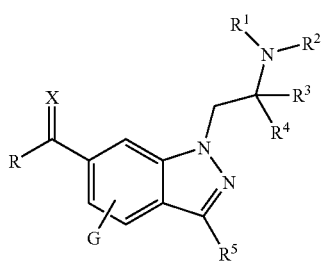

Formula I as described more fully below.

The present invention further relates to pharmaceutical compositions containing at least one compound of Formula I.

The present invention further relates to methods to lower and/or control normal or elevated intraocular pressure by administering an effective amount of a composition containing a compound of Formula I as described above.

The present invention also relates to a method for treating glaucoma which involves administering an effective amount of a composition containing a compound of Formula I as described above.

It is to be understood that both the foregoing general description and the following detailed description are exemplary and explanatory only and are intended to provide a further explanation of the present invention as claimed.

DETAILED DESCRIPTION OF THE PRESENT INVENTION

The present invention relates to compounds which are useful according to the methods of the present invention. These compounds are represented by the following Formula I:

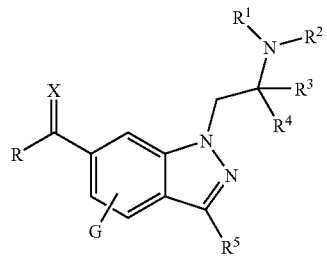

Formula I wherein G is chosen from hydrogen, halogen, or C$_{1-4}$alkyl;

R is hydroxyl, C$_1$-C$_4$ alkyl, NR$^6$R$^7$, N(R$^6$)CH$_2$(CH$_2$)$_n$N(R$^7$)(R$^8$), OC$_{1-6}$alkyl, optionally substituted with halogen or hydroxyl, wherein R$^6$, R$^7$, and R$^8$ are independently chosen from hydrogen or C$_{1-4}$alkyl, and n is 1 or 2;

X is O or CH$_2$;

R$^1$ and R$^2$ are independently chosen from hydrogen or C$_{1-4}$alkyl, or NR$^1$R$^2$ can be incorporated into a five or six membered saturated heterocyclic ring which, in the case of a six membered ring, may contain an additional heteroatom (N or O);

R$^3$ and R$^4$ are independently chosen from hydrogen, C$_{1-4}$alkyl or R$^3$, R$^4$ and the carbon atom to which they are attached can form a cyclopropyl ring, or furthermore, R$^1$ and R$^3$ together can be (CH$_2$)$_n$ to form a saturated heterocycle, where n=3-5; and R$^5$ can be hydrogen or methyl.

Pharmaceutically acceptable salts and solvates, and prodrug forms of the compounds of Formula I are also part of the present invention. Certain compounds of Formula I can contain one or more chiral centers. The present invention contemplates all enantiomers, diastereomers, and mixtures thereof.

In the above definitions, the total number of carbon atoms in a substituent group is indicated by the C$_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Preferred compounds of the present invention include compounds of Formula I wherein:

G=H or C$_{1-4}$ alkyl;

R$^1$,R$^2$=H;

R$^3$=H; and

R$^4$=C$_{1-4}$ alkyl; and pharmaceutically acceptable salts, solvates and prodrugs thereof.

Most preferred of the preferred compounds of Formula I are those wherein:

R=NR$^6$R$^7$ or OC$_{1-6}$alkyl optionally substituted with halogen or hydroxyl, wherein R$^6$ and R$^7$ are independently hydrogen or C$_{1-4}$alkyl.

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight, branched, or cyclic hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "cationic salt moiety" includes alkali and alkaline earth metal salts as well as ammonium salts.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$-$C_6$).

Synthesis

Compounds of Formula I can be prepared by using one of several synthetic. For example, desirable amides or esters of Formula I an be prepared from the appropriately substituted 3-amino-4-alkyl-benzoic acid ester, or a suitable precursor such as the corresponding 3-nitro compound [Garben et al, J. Chem. Soc. 1960, 672; Divekar et al, Can. J. Chem. 42, 63 (1964)] as outlined in Scheme 1.

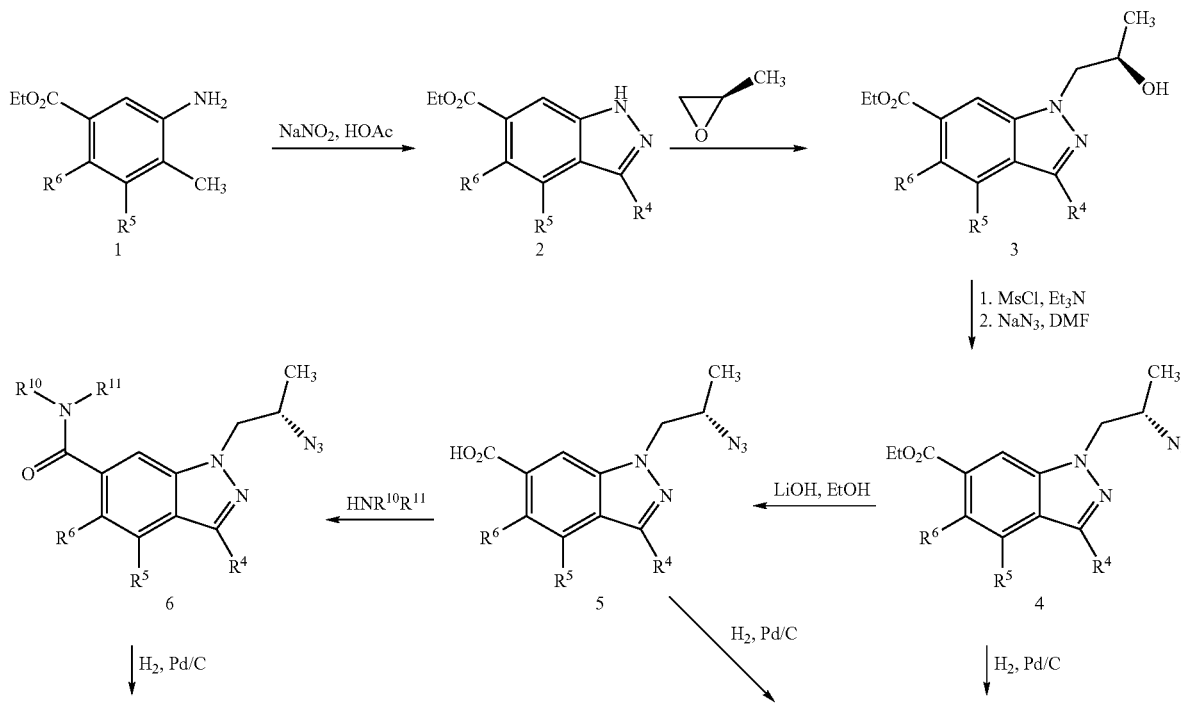

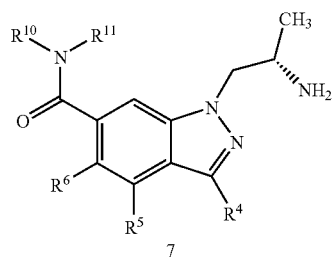

7

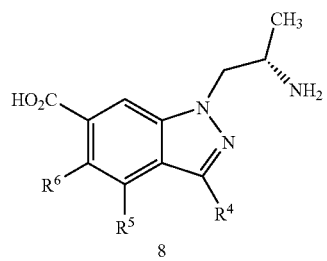

8

Using the procedures described in Scheme 1 (above), the Examples 1-2 (below), and well known procedures, one skilled in the art can prepare the compounds disclosed herein.

The following examples are given to illustrate the preparation of compounds that are the subject of this invention but should not be construed as implying any limitations to the claims. The proton magnetic resonance spectrum of each compound of the Examples was consistent with the assigned structure.

EXAMPLE 1

1-((S)-2-Aminopropyl)-1H-indazole-6-carboxylic acid ethyl ester

Step A: 1H-Indazole-6-carboxylic acid methyl ester

To a stirred solution of methyl 3-amino-4-methylbenzoate (4.98 g, 30 mmol) in acetic acid (50 mL) was added sodium nitrite (2.29 g, 33.0 mmol) in water (5 mL) dropwise at 0° C. After 5 min a solid precipitated. The cooling bath was removed and the reaction mixture was brought to room temperature. More acetic acid (50 mL) was added to dissolve the precipitate; this was stirred for 2 h, and a clear dark solution appeared. After 4 h, acetic acid was evaporated and the residue was added to a saturated aqueous sodium bicarbonate solution; this was extracted with ethyl acetate (3×60 mL). The combined extracts were washed with brine (10 mL), dried (MgSO$_4$) and evaporated. The residue solidified upon standing at room temperature to give an amorphous solid (3.9 g, 73%): MS (ES) m/z 177 (M$^+$); $^1$H NMR (CDCl$_3$): 10.05 (1H, br s), 8.29 (1H, s), 8.16 (1H, s), 7.86 (1H, d, J=8.0 Hz), 7.81 (1H, d, J=8.0 Hz), 3.97 (3H, s).

Step B: 1-((R)-2-Hydroxypropyl)-1H-indazole-6-carboxylic acid ethyl ester

To a stirred solution of the product from Step A (3.5 g, 19.8 mmol) in methanol (30 mL) was added a sodium methoxide solution in methanol (25%, 9.2 ml, 29.3 mmol) at room temperature. After 30 min, (R)-propylene oxide (2.8 mL, 39.6 mmol) was added, and the resultant solution stirred for 3 h. The solution was diluted with saturated aqueous solution of ammonium chloride (20 mL) and extracted with ethyl acetate (3×65 mL). The combined extract was washed with brine (10 mL), dried (MgSO$_4$) and evaporated to give a residue which was subjected to chromatography (silica, 30% ethyl acetate in hexane to 50% ethyl acetate in hexane) to give an oil (1.8 g, 39%): MS (ES) m/z 235 (M$^+$); $^1$H NMR (CDCl$_3$) 8.20 (1H, s), 8.07 (1H, s), 7.84 1H, d, J=7.2 Hz), 7.81 (1H, d, J=7.2 Hz), 4.47 (2H, dd, J=7.2 Hz), 4.34 (2H, m), 3.20 (1H, m), 1.44 (3H, t, J=7.2 Hz). 1.31 (3H, d, J=6.4 Hz).

Step C: 1-(2-Azidopropyl)-1H-indazole-6-carboxylic acid ethyl ester

To a stirred solution of the product from Step B (1.8 g, 7.6 mmol) in dichloromethane (10 mL) was added triethylamine (1.3 mL, 9.2 mmol) followed by methanesulfonyl chloride (0.72 mL, 9.2 mmol) at 0° C. After 30 min, ether (50 mL) was added followed by water (50 mL). The organic layer was separated and the aqueous was extracted with ether (2×50 mL). The combined organic layers were washed with brine (30 mL), dried and evaporated. The residue was taken up in DMF (20 mL) and sodium azide (0.99 g, 15.2 mmol) was added. The reaction mixture was heated at 70° C. for 14 h, poured into water, and extracted with ether (3×50 mL). The combined extracts were washed with brine, dried and evaporated. The residue was purified by chromatography (silica, hexane to 10% ethyl acetate in hexane) to give an oil (1.75 g, 83%): MS (ES) m/z 274 (M$^+$); $^1$H NMR (CDCl$_3$) 8.22 (1H, s), 8.09 (1H, s), 7.84 (1H, d, J=1.2 Hz), 7.78 (1H, d, J=1.2 Hz), 4.45 (4H, m), 4.24 (1H, m), 1.46 (3H, t, J=7.2 Hz). 1.35 (3H, d, J=6.8 Hz).

Step D: 1-((S)-2-Aminopropyl)-1H-indazole-6-carboxylic acid ethyl ester

To a solution of the product from Step C (0.20 g, 0.73 mmol) in ethanol (10 mL) was added Pd/C (10%, 0.01 g) under nitrogen atmosphere at room temperature. The resultant suspension was stirred for 18 h under hydrogen atmosphere. The reaction was filtered through a filter aide and the filtrate was concentrated in vacuo to give a residue (0.12 g, 66%) which was purified by chromatography (silica, 10% ethyl acetate in hexane). The oil was converted to the fumaric acid salt and crystallized from methanol/ether to give a solid (0.10 g): mp 150-152° C.; MS (ES) m/z 248 (M$^+$); $^1$H NMR (DMSO-d$_6$) 8.38 (1H, s), 8.24 (1H, d, J=0.8 Hz), 7.89 (1H, d, J=9.2 Hz), 7.70 (1H, d, J=9.2 Hz), 6.46 (2H, s), 4.44 (2H, m), 4.39 (2H, dd, J=6.8 Hz), 3.60 (1H, m), 1.36 (3H, t, J=7.2 Hz), 1.11 (3H, d, J=6.4 Hz). Analysis. Calculated for C$_{13}$H$_{17}$N$_3$O$_2$.C$_4$H$_4$O$_4$.0.5H$_2$O: C, 54.83; H, 5.95; N, 11.28. Found: C, 54.77; H, 5.95; N, 11.46.

EXAMPLE 2

1-((S)-2-Aminopropyl)-1H-indazole-6-carboxylic acid amide

Step A: 1-((S)-2-Azidopropyl)-1H-indazole-6-carboxylic acid

To a stirred solution of the product from Step 3, Example 1 (0.52 g, 1.80 mmol) in ethanol (10 mL) was added lithium hydroxide (0.16 g, 3.75 mmol) in water (3 mL) at room temperature. After 16 h, ethanol was evaporated and to the residue was added a solution of saturated aqueous ammonium chloride (20 mL) and ethyl acetate. The organic layer was separated and the aqueous was extracted with ethyl acetate (2×50 mL). The combined extracts were washed with brine (30 mL), dried and evaporated. The residue was purified by chromatography (silica, 50% ethyl acetate in hexane to ethyl acetate) to give an oil (0.40 g, 91%): MS (ES) m/z 246 (M$^+$).

Step B: 1-((S)-2-Azidopropyl)-1H-indazole-6-carboxylic acid amide

To the product from Step A (0.17 g, 0.64 mmol) in DMF (5 mL) was added HOBT (0.041 g, 0.30 mmol), and EDCI (0.18 g, 0.96 mmol), followed by a solution of ammonia in dioxane (0.5 M, 0.18 g, 0.96 mmol). After 18 h, a saturated aqueous solution of ammonium chloride (20 mL) was added. The mixture was extracted with ethyl acetate (3×50 mL) and the combined extracts were washed with brine, dried and evaporated. The residue was purified by chromatography (silica, 50% ethyl acetate in hexane, ethyl acetate) to give an oil (0.14 g, 92%): MS (ES) m/z 245 (M$^+$); $^1$H NMR (CDCl$_3$) 8.11 (1H, s), 8.08 (1H, s), 7.81 (1H, d, J=8.0 Hz), 7.52 (1H, d, J=8.0 Hz), 4.43 (2H, m), 4.15 (1H, m), 1.36 (3H, d, J=8.0 Hz).

Step C: 1-((S)-2-Aminopropyl)-1H-indazole-6-carboxylic acid amide

To a solution of the product from Step B (0.14 g, 0.55 mmol) in ethanol (10 mL) was added Pd/C (10%, 0.01 g) under a nitrogen atmosphere at room temperature. The resultant suspension was stirred for 18 h under a hydrogen atmosphere. The reaction was filtered through a filter aide and the filtrate was concentrated in vacuo to give a solid (0.09 g, 75%): mp 170-172° C.; MS (ES) m/z 219 (M$^+$); $^1$H NMR (DMSO-d$_6$) 8.25 (1H, s), 8.12 (1H, s), 8.04 (1H, br s), 7.80 (1H, d, J=8.0 Hz), 7.63 (1H, d, J=8.0 Hz), 7.44 (1H, s), 4.27 (2H, m), 3.34 (1H, m), 0.96 (3H, d, J=6.0 Hz). Analysis. Calculated for C$_{11}$H$_{14}$N$_4$O: C, 60.53; H, 6.47; N, 25.67. Found: C, 60.37; H, 6.33; N, 25.48.

The compounds of the present invention can be used to lower and control IOP including IOP associated with normotension glaucoma, ocular hypertension, and glaucoma in warm blooded animals including humans and other mammals. Since the treatment of glaucoma is preferably with compounds that do not enter the CNS, relatively polar compounds that are 5-HT$_2$ agonists are of particular interest. The compounds are preferably formulated in pharmaceutical compositions which are preferably suitable for topical delivery to the eye of the patient.

The compounds of this invention, Formula I, can be incorporated into various types of pharmaceutical compositions, such as ophthalmic formulations for delivery to the eye (e.g., topically, intracamerally, or via an implant). The compounds are preferably incorporated into topical ophthalmic formulations for delivery to the eye. The compounds may be combined with opthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an opthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8, and more preferably from about 6.5 to about 7.5. The compounds will normally be contained in these formulations in an amount 0.001% to 5% by weight, but preferably in an amount of 0.025% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α$_1$ antagonists (e.g., nipradolol), α$_2$ agonists (e.g. iopidine and brimonidine), miotics (e.g., pilocarpine and epinephrine), prostaglandin analogs (e.g., latanoprost, travoprost, unoprostone, and compounds set forth in U.S. Pat. Nos. 5,889,052; 5,296,504; 5,422,368; and 5,151,444, "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO 94/13275, including memantine.

The compounds of the present invention preferably function as 5-HT$_2$ agonists and preferably do not enter the CNS. Compounds having the ability to be a 5-HT$_2$ agonist are beneficial for controlling IOP as well as the treatment of glaucoma as shown in U.S. Pat. No. 6,664,286 incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma. Pharmaceutically acceptable amounts of the compounds of the present invention will be readily understood by those skilled in the art to mean amounts sufficient to effect the desired therapy without toxicity or other deleterious effects on the patients' health. Examples of such amounts include without limitation those amounts shown in the Examples.

Another embodiment of the present invention is a method of activating or binding serotonin receptors, comprising administering an effective amount of at least one compound of the present invention to a patient using an amount effective to activate or bind serotonin receptors, wherein such amount includes, but is not limited to, the dosage levels described herein.

The procedures described herein in Method 1 can be used to confirm a compound's 5-HT$_2$ binding affinity.

Method 1

5-HT$_2$ Receptor Binding Assay

To determine the affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 µL) dispersed in 50 mM Tris HCl buffer (pH 7.4) are incubated with [$^{125}$I]DOI (80 pM final) in the absence or presence of methiothepin (10 µM final) to define total and non-specific binding, respectively, in a total volume of 0.5 mL. The assay mixture is incubated for 1 hour at 23° C. in polypropylene tubes and the assays terminated by rapid vacuum filtration over Whatman GF/13 glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ or K$_i$ value.

Method 2

5-HT$_2$ Functional Assay: [Ca$^{2+}$]$_i$ Mobilization

The receptor-mediated mobilization on intracellular calcium ([Ca$^{2+}$]$_i$) was studied using the Fluorescence Imaging Plate Reader (FLIPR) instrument. Rat vascular smooth muscle cells, A7r5, were grown in a normal media of DMEM/10% FBS and 10 µg/mL gentamycin. Confluent cell monolayers were trypsinized, pelleted, and re-suspended in normal media. Cells were seeded in a 50 µL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 mL) to each well of the 96-well plate and incubated with dye for 1 h at 23° C.

Typically, test compounds were stored at 25 µM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 µM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000-12000 counts by modifying the exposure time, the camera F-stop, or the laser power. Instrument settings for a typical assay were the following: laser power 0.3-0.6 W, camera F-stop F/2, and exposure time 0.4 sec. An aliquot (25 µL) of the test compound was added to the existing 100 µL dye-loaded cells at a dispensing speed of 50 µL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response [E$_{max}$%]. When the compounds were tested as antagonists against 10 µM 5-HT, they were incubated with the cells for 15 minutes prior to the addition of 5-HT.

Using the foregoing methods, 5-HT$_2$ binding affinities and agonist potential can readily be determined.

The above procedures were used to generate the data shown in Table 1.

TABLE 1

5-HT$_{2A}$ Receptor Binding and Functional Data

| | 5-HT$_{2A}$ | | |
|---|---|---|---|
| Example | IC$_{50}$ nM | EC$_{50}$ nM | E$_{max}$ |
| 1 | 10 | 837 | 86 |
| 2 | 5.9 | 465 | 90 |

The following topical ophthalmic formulations are useful according to the present invention administered 1-4 times per day according to the discretion of a skilled clinician.

EXAMPLE 3

| Ingredients | Amount (wt %) |
|---|---|
| Compound of Example 1-2 | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 4

| Ingredients | Amount (wt %) |
|---|---|
| Compound of Example 1-2 | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 5

| Ingredients | Amount (wt %) |
|---|---|
| Compound of Example 1-2 | 0.01-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 6

| Ingredients | Amount (wt %) |
|---|---|
| Compound of Example 1-2 | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A compound of Formula I:

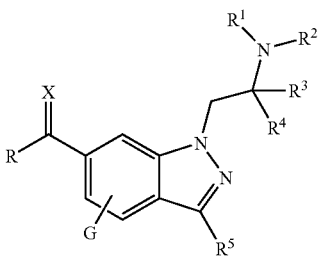

wherein G is chosen from hydrogen, halogen, or $C_{1-4}$alkyl;
R is hydroxyl, $C_1$-$C_4$ alkyl, $NR^6R^7$, $N(R^6)CH_2(CH_2)_nN(R^7)(R^8)$, $OC_{1-6}$alkyl, optionally substituted with halogen, hydroxyl, wherein $R^6$, $R^7$, and $R^8$ are independently hydrogen or $C_{1-4}$alkyl, and n is 1 or 2;
X is O or $CH_2$;
$R^1$ and $R^2$ are independently hydrogen or $C_{1-4}$alkyl, or $NR^1R^2$ can be incorporated into a five or six membered saturated heterocyclic ring which, in the case of a six membered ring, may contain an additional heteroatom selected from N and O;
$R^3$ and $R^4$ are independently chosen from hydrogen, $C_{1-4}$alkyl or $R^3$, $R^4$ and the carbon atom to which they are attached can form a cyclopropyl ring, or, $R^1$ and $R^3$ together can be $(CH_2)_n$ to form a saturated where n=3-5; and
$R^5$ is hydrogen or methyl; and
pharmaceutically acceptable salts thereof.

2. The compound of claim 1, wherein for Formula I:
G=H or $C_{1-4}$ alkyl;
$R^1$,$R^2$=H
$R^3$=H; and
$R^4$=$C_{1-4}$ alkyl.

3. The compound of claim 2, wherein for Formula I:
R=$NR^6R^7$ or $OC_{1-6}$alkyl optionally substituted with halogen or hydroxyl, wherein $R^6$ and $R^7$ are independently hydrogen or $C_{1-4}$alkyl.

4. The compound of claim 2 that is: 1-((S)-2-Aminopropyl)-1H-indazole-6-carboxylic acid ethyl ester and pharmaceutically acceptable salts thereof.

5. A topical ophthalmic composition comprising a pharmaceutically effective amount of a compound in an ophthalmically acceptable vehicle, wherein the compound is of Formula I:

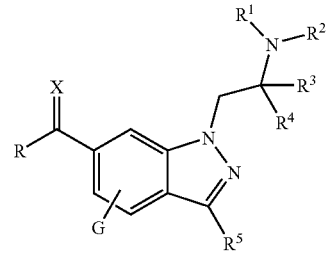

wherein G is chosen from hydrogen, halogen, or $C_{1-4}$alkyl;
R is hydroxyl, $C_1$-$C_4$ alkyl, $NR^6R^7$, $N(R^6)CH_2(CH_2)_nN(R^7)(R^8)$, $OC_{1-6}$alkyl, optionally substituted with halogen, hydroxyl, wherein $R^6$, $R^7$, and $R^8$ are independently hydrogen or $C_{1-4}$alkyl, and n is 1 or 2;
X is O or $CH_2$;
$R^1$ and $R^2$ are independently hydrogen or $C_{1-4}$alkyl, or $NR^1R^2$ can be incorporated into a five or six membered saturated heterocyclic ring which, in the case of a six membered ring, may contain an additional heteroatom selected from N and O;
$R^3$ and $R^4$ are independently chosen from hydrogen, $C_{1-4}$alkyl or $R^3$, $R^4$ and the carbon atom to which they are attached can form a cyclopropyl ring, or, $R^1$ and $R^3$ together can be $(CH_2)_n$ to form a saturated where n=3-5; and
$R^5$ is hydrogen or methyl; and
pharmaceutically acceptable salts thereof.

6. The ophthalmic composition of claim 5, wherein for the compound of Formula I:
G=H or $C_{1-4}$ alkyl;
$R^1$,$R^2$H
$R^3$=H; and
$R^4$=$C_{1-4}$ alkyl.

7. The ophthalmic composition of claim 6, wherein for the compound of Formula I:
R=$NR^6R^7$ or $OC_{1-6}$alkyl optionally substituted with halogen or hydroxyl,
wherein $R^6$ and $R^7$ are independently hydrogen or $C_{1-4}$alkyl.

* * * * *